United States Patent
Jingu et al.

(10) Patent No.: US 8,587,777 B2
(45) Date of Patent: Nov. 19, 2013

(54) EXAMINATION METHOD AND EXAMINATION DEVICE

(75) Inventors: Takahiro Jingu, Takasaki (JP); Kazuo Takahashi, Ninomiya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 188 days.

(21) Appl. No.: 13/202,708

(22) PCT Filed: Nov. 19, 2009

(86) PCT No.: PCT/JP2009/006212
§ 371 (c)(1),
(2), (4) Date: Aug. 22, 2011

(87) PCT Pub. No.: WO2010/106596
PCT Pub. Date: Sep. 23, 2010

(65) Prior Publication Data
US 2011/0299088 A1    Dec. 8, 2011

(30) Foreign Application Priority Data

Mar. 19, 2009   (JP) .................................. 2009-067238

(51) Int. Cl.
*G01N 21/00*   (2006.01)
*G06F 19/00*   (2011.01)

(52) U.S. Cl.
USPC .......................................... 356/237.1; 702/40

(58) Field of Classification Search
USPC .............. 356/237.1–237.5, 73; 382/149, 226; 702/35–40, 64, 81
See application file for complete search history.

(56) References Cited

U.S. PATENT DOCUMENTS

| 4,820,932 A * | 4/1989 | Miller ...................... 250/559.06 |
| 2004/0066507 A1* | 4/2004 | Kren et al. .................. 356/237.4 |
| 2004/0246476 A1 | 12/2004 | Bevis et al. |

(Continued)

FOREIGN PATENT DOCUMENTS

| JP | 63-298035 | 12/1988 |
| JP | 7-113759 | 5/1995 |

(Continued)

OTHER PUBLICATIONS

Japanese Office Action, and partial English translation thereof, issued in Japanese Patent Application No. 2009-067238 dated Aug. 7, 2012.

(Continued)

*Primary Examiner* — Hoa Pham
(74) *Attorney, Agent, or Firm* — McDermott Will & Emery LLP

(57) ABSTRACT

A change in surface state can be dealt with by setting threshold values different for respective regions of an object to be examined in accordance with a magnitude of noises, thereby improving a detection sensitivity. A function for setting an examination threshold value every region is installed. A function for setting examination threshold values every plurality of detectors spatially independent of each other is installed. The magnitude of noises from the object to be examined differs depending on a spatial direction even in the same region. Therefore, the detection sensitivity is maximized by maximizing an S/N ratio of a detection signal by an optimum signal arithmetic operating process according to the magnitude of noises from the object to be examined every detector and every region of the object to be examined and by setting the optimum threshold values.

12 Claims, 9 Drawing Sheets

(56) References Cited

U.S. PATENT DOCUMENTS

| | | | |
|---|---|---|---|
| 2005/0092899 A1* | 5/2005 | Wolf et al. | 250/214 R |
| 2006/0256326 A1* | 11/2006 | Bills et al. | 356/237.2 |
| 2008/0013084 A1* | 1/2008 | Matsui et al. | 356/237.5 |
| 2008/0075352 A1* | 3/2008 | Shibuya et al. | 382/141 |
| 2008/0239292 A1* | 10/2008 | Kawaki et al. | 356/73 |
| 2012/0312104 A1* | 12/2012 | Hamamatsu et al. | 73/865.8 |

FOREIGN PATENT DOCUMENTS

| | | |
|---|---|---|
| JP | 9-304289 | 11/1997 |
| JP | 2000-105203 A | 4/2000 |
| JP | 2002-513461 A | 5/2002 |
| JP | 2004-177284 A | 6/2004 |
| JP | 2005-283190 A | 10/2005 |
| JP | 2007-526444 | 9/2007 |

OTHER PUBLICATIONS

Japanese Office Action issued in Japanese Application No. 2009-067238 dated Apr. 16, 2013 with English Translation.

* cited by examiner

1···LIGHT SOURCE 2···AMOUNT-OF-LIGHT ADJUSTING MECHANISM
3···OPTICAL AXIS ADJUSTING MECHANISM 5···ZOOM MECHANISM
6a, 6b, 6c···MIRROR 7a, 7b···FOCUSING LENS 8···SAMPLE 9···XYZ θ STAGE
10···DETECTION LENS 11···DETECTOR 12···A/D CONVERTER
13···FOREIGN MATTER/DEFECT DETERMINING MECHANISM
14···SIGNAL PROCESSING UNIT 131···INPUT UNIT 132···OUTPUT UNIT

FIG. 7
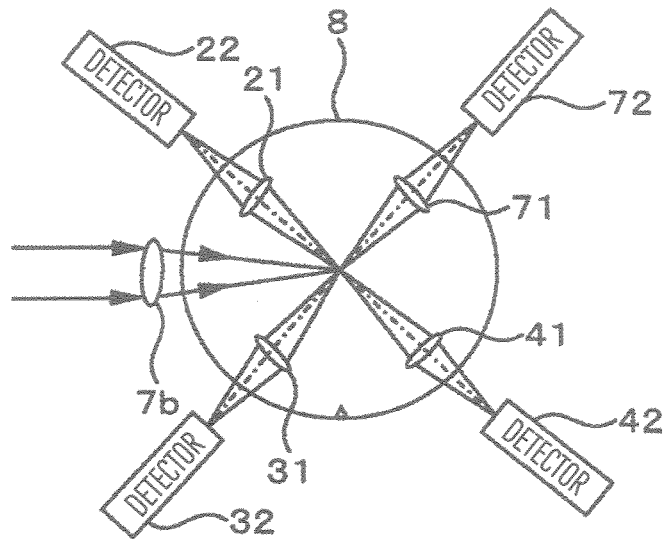
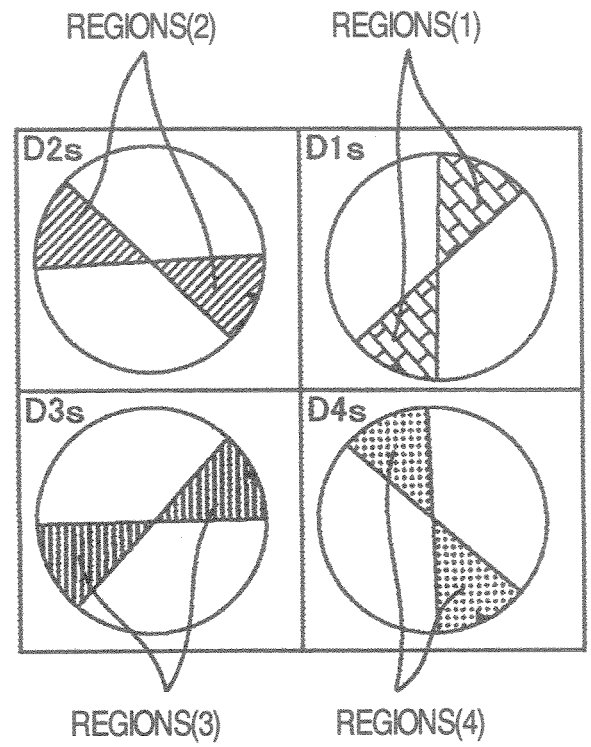

EXAMINATION METHOD AND EXAMINATION DEVICE

RELATED APPLICATIONS

This application is the U.S. National Phase under 35 U.S.C. §371 of International Application No. PCT/JP2009/006212, filed on Nov. 19, 2009, which in turn claims the benefit of Japanese Application No. 2009-067238, filed on Mar. 19, 2009, the disclosures of which Applications are incorporated by reference herein.

TECHNICAL FIELD

This invention relates to an examination technique of an optical examination device. For example, the invention relates to an examination method of examining a foreign matter, a defect, or the like on the surface of a semiconductor wafer in a manufacturing step of a semiconductor device, an examination device for examining a foreign matter, a defect, or the like, and an examination method and an examination device of the semiconductor device. This invention also relates to an examination method and an examination device of a disk or a glass substrate other than a wafer.

BACKGROUND ART

In an optical examination device in the related art, an examination threshold value is set in accordance with a magnitude of scattering light from an object to be examined. However, a same value is generally set for the whole surface of the object to be examined. A common threshold value is used among a plurality of detectors. For example, Patent Literatures 1 and 2 can be mentioned as techniques regarding those techniques.

CITATION LIST

Patent Literature

Patent Literature 1: Official Gazette of JP-A-9-304289
Patent Literature 2: Official Gazette of JP-A-7-113759

SUMMARY OF INVENTION

Technical Problem

However, a state of the actual surface of the object to be examined is not uniform. According to a uniform examination threshold value for the whole surface of the object to be examined, there is such a problem that it is subjected to a restriction of a region having the largest noises and it results in a deterioration of a detection sensitivity of a region having small noises.

It is an object of this invention to provide an examination method or an examination device which can cope with a change in surface state of an object to be examined and can improve a detection sensitivity.

Solution to Problem

One feature of the invention relates to an examination device comprising: an illuminating system for illuminating illumination light to an object to be examined; a detecting unit for detecting scattering light from the object to be examined; a plurality of detectors which are spatially independent of each other; and a signal processing unit for processing each output signal of the plurality of detectors by an independent processing condition.

Another feature of the invention relates to an examination method of illuminating illumination light to an object to be examined and examining the object, comprising the steps of: detecting scattering light from the object to be examined by a plurality of detectors which are spatially independent of each other; and processing each output signal of the plurality of detectors by an independent processing condition.

The above and other features of the invention will be further described in the following description.

Advantageous Effects of Invention

According to one aspect of the invention, the examination device which can cope with a change in surface state of the object to be examined and can improve a detection sensitivity is provided.

According to another aspect of the invention, the examination method which can cope with a change in surface state of an object to be examined and can improve a detection sensitivity is provided.

BRIEF DESCRIPTION OF DRAWINGS

[FIG. 7] Explanatory diagram showing an example of an optical system construction in the case of four detectors and distribution of reflection/scattering light from a sample in the embodiment of the invention.

DESCRIPTION OF EMBODIMENTS

Embodiments of the invention will now be described hereinbelow by using the drawings.

Embodiment 1

Figure 1:
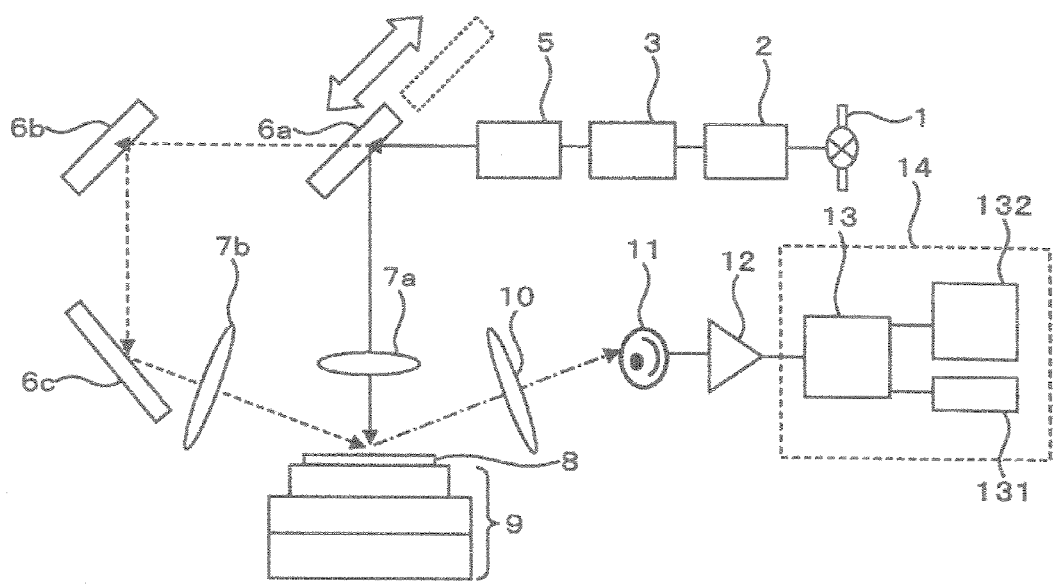
[FIG. 1] Explanatory diagram showing an example of a device construction of a surface examination device in an embodiment of the invention.

An example of a device construction of a surface examination device according to an embodiment of the invention is shown in FIG. 1. Light irradiated from a light source 1 passes through an amount-of-light adjusting mechanism 2 which can adjust a brightness, an optical axis compensating mechanism 3, and a zoom mechanism 5 and is irradiated to a sample 8 as an object to be examined. The light irradiated from the zoom mechanism 5 is switched to a vertical optical path or an oblique optical path by a vertical/oblique irradiation switching mirror 6a. The light branched vertically is focused by a focusing lens 7a and is irradiated to the sample 8. The sample 8 is put on an XYZθ stage 9. The XYZθ stage is constructed so as to be movable in each axial direction of an X axis and a Y axis which are parallel with the surface of the sample, a Z axis which is perpendicular to the sample surface, and a θ axis which enables the sample to be rotated. Generally, the XYZθ stage is used for focal adjustment to form an image of the irradiated light by the motion in the Z-axis direction. During the surface examination scanning, a spot of the light irradiated to the sample surface moves spirally from the center of the object to be examined such as a wafer or the like toward the outer periphery or from the outer periphery toward the center by the movement in the θ-axis direction and the X-axis or Y-axis direction. During the surface examination scanning, the spot of the light irradiated to the sample surface moves concentrically from the center of the object to be examined such as a wafer or the like toward the outer periphery or from the outer periphery toward the center by the movement in the θ-axis direction and the X-axis or Y-axis direction. The reflection/scattering light from the sample 8 by the irradiated light is guided to a detector 11 by a detection lens 10. After that, a signal of the detected light is digitally encoded by an A/D converter 12. After that, the signals due to the reflection/scattering light from the sample 8 and from a foreign matter/defect are distinguished/discriminated by a foreign matter/defect determining process by a foreign matter/defect determining mechanism 13, thereby detecting the foreign matter/defect. An input unit 131 such as keyboard, mouse, or the like and an output unit 132 such as display, printer, or the like are connected to the foreign matter/defect determining mechanism 13. If there are a plurality of detectors 11 as shown in FIG. 2, which will be described hereinafter, the output unit 132 may be constructed so that signals of a plurality of detectors and signal processing results can be arbitrarily selected and displayed into a same display screen of the display or the like.

Figure 2:
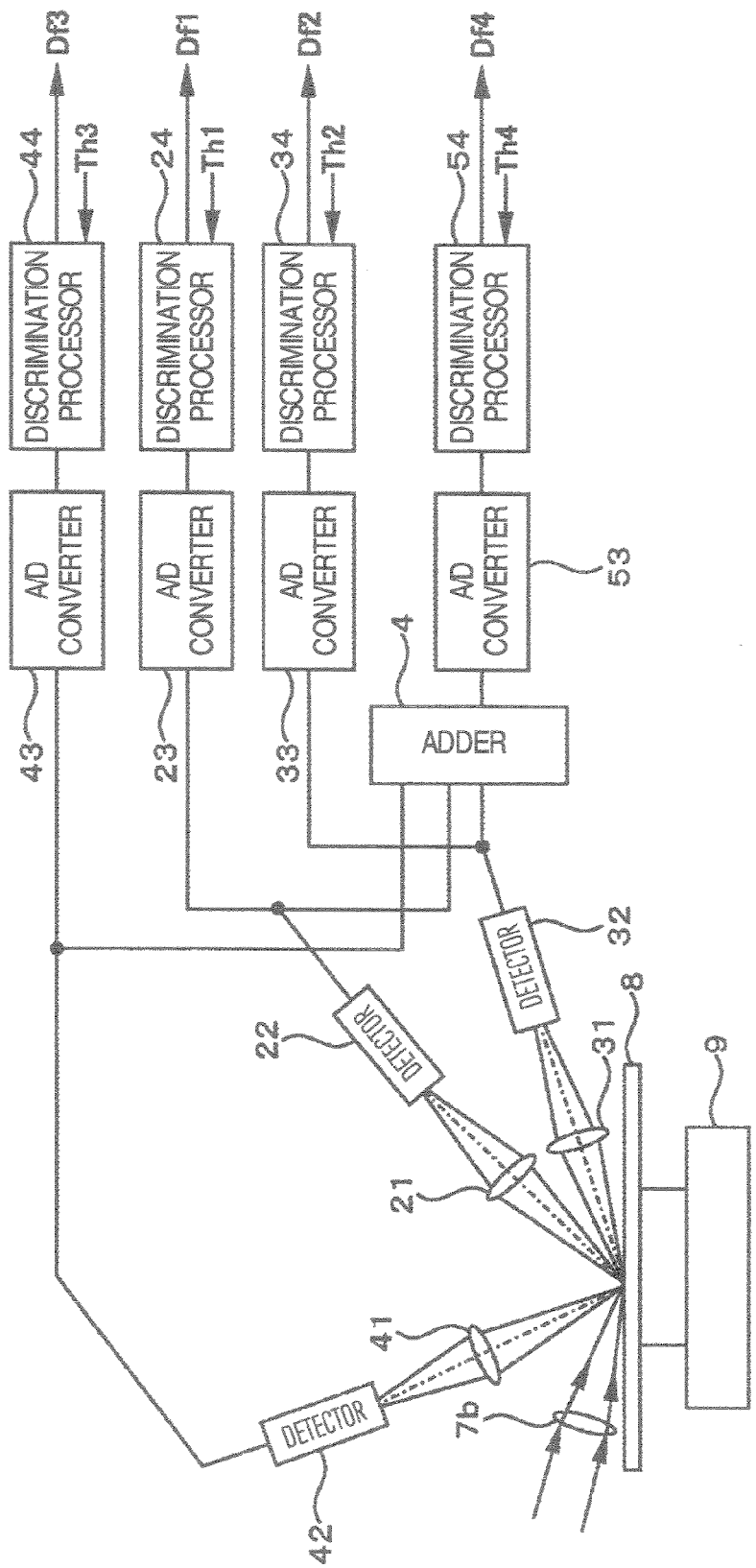
[FIG. 2] Explanatory diagram showing an example of a construction of detectors which are spatially independent of each other and a signal process in the embodiment of the invention.

An example of a construction of a plurality of detectors which are spatially independent of each other and a signal process is shown in FIG. 2. In this example, the number of detectors is set to 3. The reflection/scattering light from the sample 8 is guided to photoelectric converting surfaces of detectors 22, 32, and 42 by detection lenses 21, 31, and 41, respectively. Four kinds of signals are formed from three outputs of the detectors 22, 32, and 42 and an output of an adder 4. Those signals are digitally encoded by A/D converters 23, 33, 43, and 53. After that, the signals by the reflection/scattering light from the foreign matter/defect are distinguished/discriminated by discrimination processors 24, 34, 44, and 54 on the basis of different threshold values Th1, Th2, Th3, and Th4. Results Df1, Df2, Df3, and Df4 are outputted.

Figure 3:
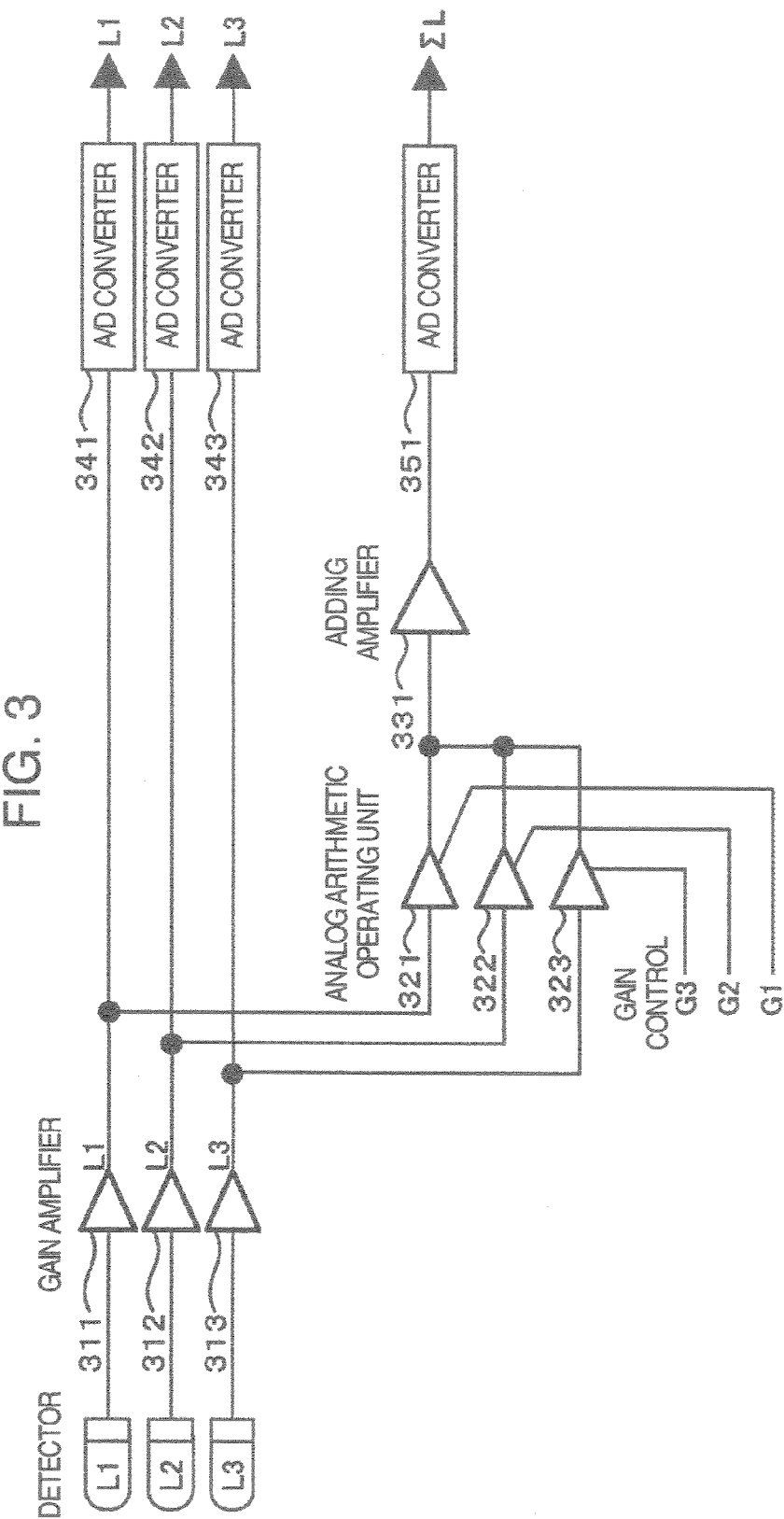
[FIG. 3] Explanatory diagram showing an example of a function and a construction of an adder 4 in the embodiment of the invention.

An example of a function and a construction of the adder 4 is shown in FIG. 3. In this example, three detectors L1, L2, and L3 are used. Outputs of the detectors L1, L2, and L3 are transmitted through gain amplifiers 311, 312, and 313 and A/D converters 341, 342, and 343 and become outputs L1, L2, and L3, respectively. Further, the outputs of the gain amplifiers 311, 312, and 313 are transmitted through gain amplifiers 321, 322, and 323, are inputted to an adding amplifier 331, are transmitted through an A/D converter 351, and become an output ΣL. With respect to the gain amplifiers 321, 322, and 323, gain values G1, G2, and G3 are set for detection signals of the respective detector so as to maximize an S/N ratio of an addition signal of the outputs of the detectors L1, L2, and L3.

Figure 4:
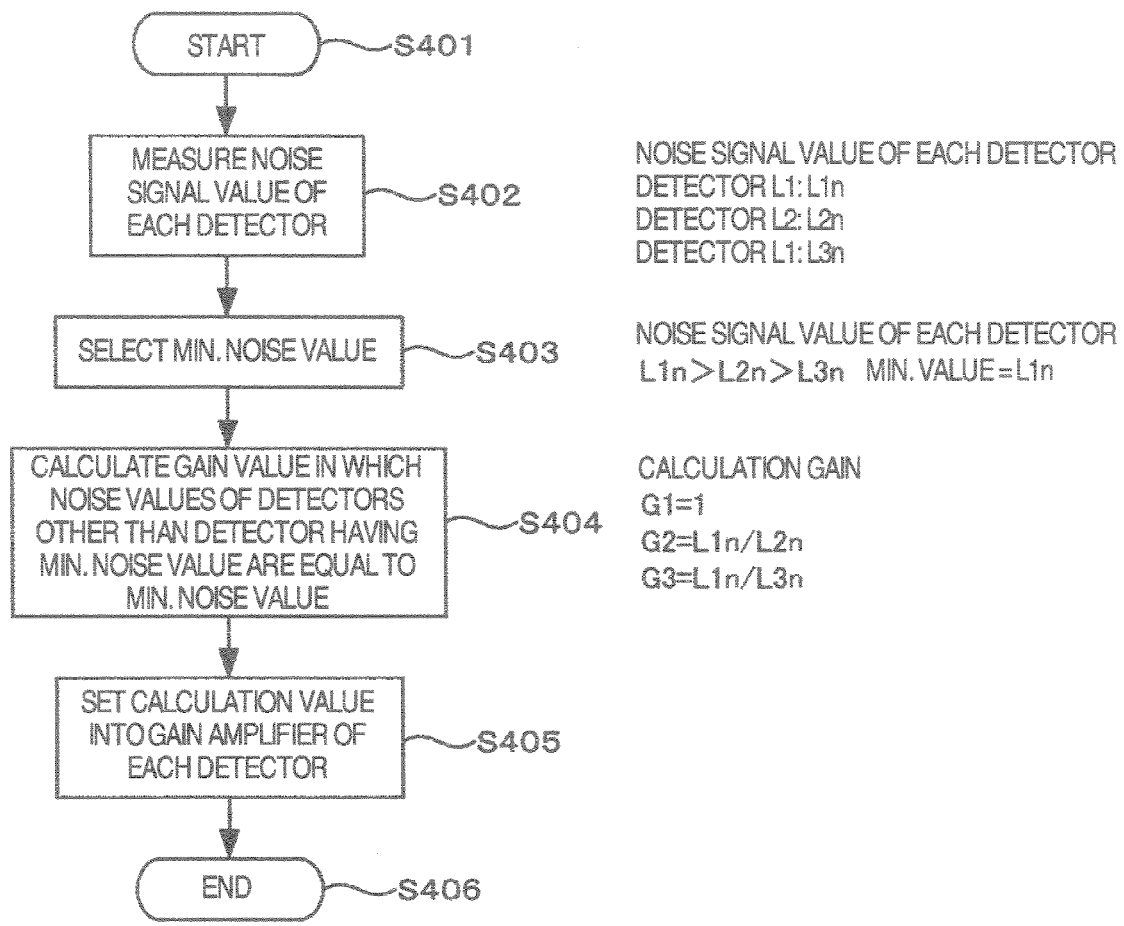
[FIG. 4] Explanatory diagram showing an example of a calculation processing procedure of gain values G1, G2, and G3 for maximizing an S/N ratio of an addition signal shown in FIG. 3.

An example of a calculation processing procedure of the gain values G1, G2, and G3 for maximizing the S/N ratio of the addition signal shown in FIG. 3 is shown in FIG. 4. When the process is started (step 401; in the diagram, referred to as S401, and so on), noise signal values L1n, L2n, and L3n of the detectors are measured (step 402). Among them, the noise value of the minimum value is selected (step 403). In this example, it is assumed to be L1n. As for a gain to be set, the minimum value is set to a reference=1 and the noise values of the remaining detection signals are set to the same value as L1n. In this example, it is calculated so that G1=1 (reference), G2=L1n/L2n, and G3=L1n/L3n (step 404). A calculation value is set into the gain amplifier of each detector (S405) and the processing routine is finished (step 406).

Figure 5:
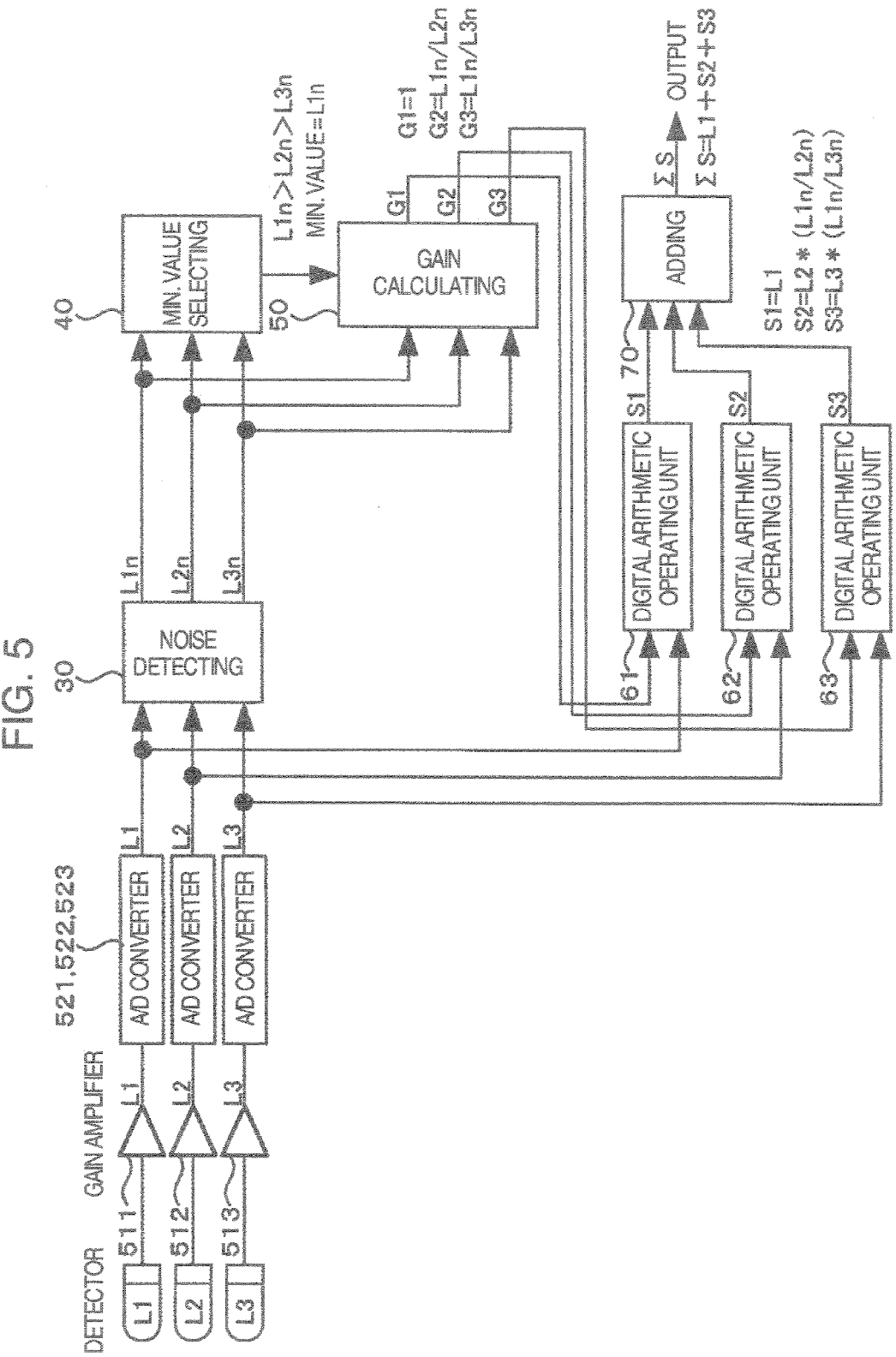
[FIG. 5] Explanatory diagram showing an example of a function and a construction of a process in the case of using digital data in the embodiment of the invention.

An example of a function and a construction of a process in the case of using digital data is shown in FIG. 5. The outputs of the detectors L1, L2, and L3 are transmitted through gain amplifiers 511, 512, and 513 and A/D converters 521, 522, and 523 and become outputs L1, L2, and L3, respectively. Further, the outputs L1, L2, and L3 become noise detection signals L1n, L2n, and L3n by a noise detecting circuit 30 and are inputted to a minimum value detecting circuit 40 and a gain calculating circuit 50. On the basis of the minimum value selected by the minimum value selecting circuit 40 (in the example of FIG. 5, since L1n>L2n>L3n, L1n is selected as a minimum value), a gain calculating process is executed and gain signals G1, G2, and G3 are calculated in the gain calculating circuit 50. In the example of FIG. 5, G1=1, G2=L1n/L2n, and G3=L1n/L3n. In gain arithmetic operating circuits 61, 62, and 63, the outputs L1, L2, and L3 and the gain signals G1, G2, and G3 are inputted thereto, gain arithmetic operating processes are executed on the basis of them, and output signals S1, S2, and S3 are outputted. In the example of FIG. 5, S1=L1, S2=L2*(L1n/L2n), and S3=L3*(L1n/L3n). In an adding circuit 70, those output signals S1, S2, and S3 are added and outputted as ΣS. ΣS=S1=L1+S2+S3. Although a logic for maximizing the S/N ratio of the addition signal of the detectors is substantially the same as that shown in FIG. 4, in the processing circuit in the analog signals in FIG. 3, it is necessary to previously measure noise values of the detectors and calculate and set the gain values. However, in the construction of FIG. 5, since the gain values for maximizing the S/N ratio of the addition signal of the detectors can be calculated in a real-time manner, the gain values can be set for the finer regions and the improvement of a detection sensitivity can be realized.

Figure 6:
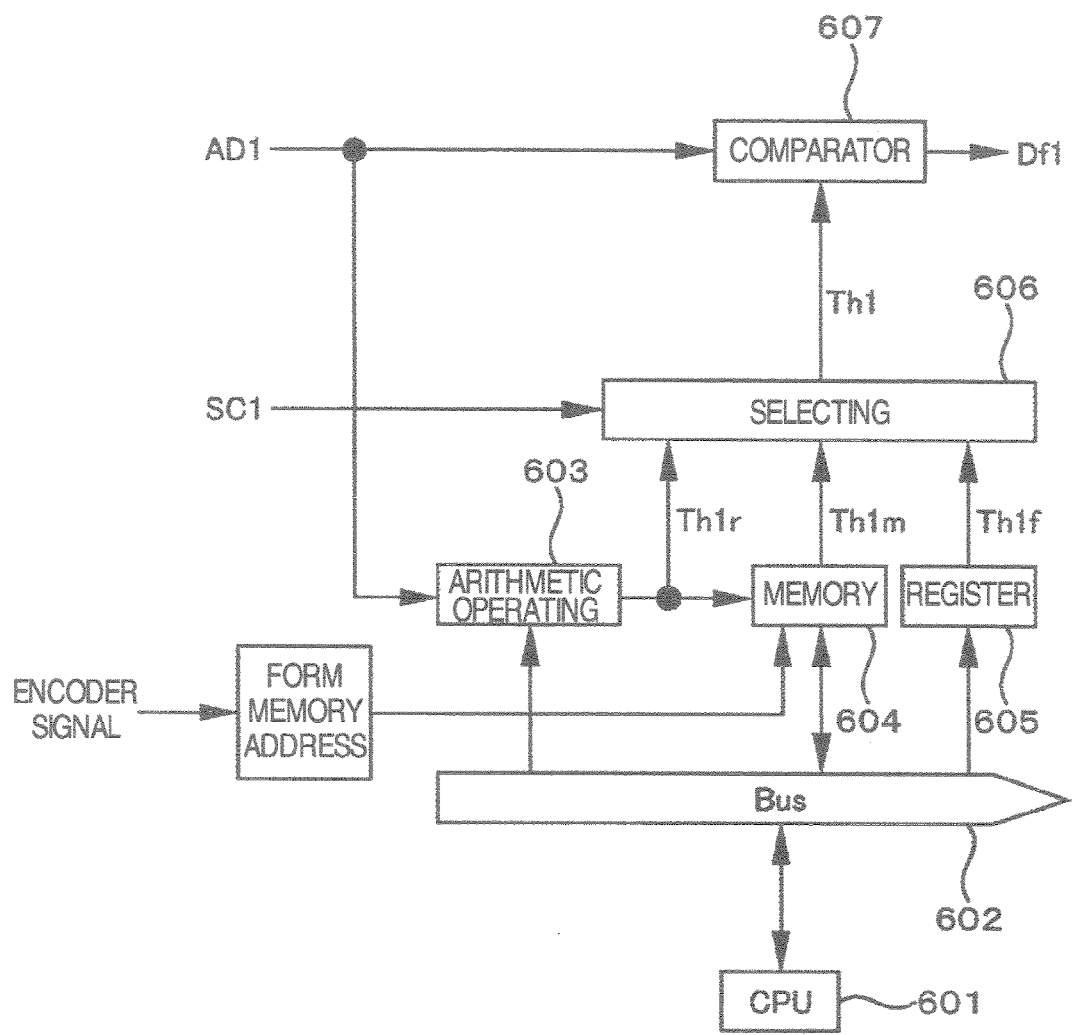
[FIG. 6] Explanatory diagram showing an example of a function and a construction of a discrimination processor in the embodiment of the invention.

An example of a function and a construction of the discrimination processor is shown in FIG. 6. An output AD1 of the A/D converter is inputted to an arithmetic operating unit 603. A threshold value Th1r is calculated in accordance with a preset arithmetic operating logic or an arithmetic operating logic which has been set through a bus 602 by an instruction of a CPU 601 and can be stored into a memory 604. A creation of a memory address at the time of writing the threshold value Th1r and at the time of reading out a threshold value Th1m is performed on the basis of a signal of an encoder equipped in an examination stage. In accordance with the memory address, an examining position is recognized and the writing of the calculated threshold value corresponding to the examining position into the memory 604 and the reading-out of the examination threshold value at the time of the examination are performed. The reading-out and writing from/into the memory 604 can be performed through the bus 602 by an instruction of the CPU 601. A threshold value Th1$f$ can be set into a register 605 through the bus 602 by an instruction of the CPU 601. When the threshold value is inputted to a comparator 607, one of Th1$r$, Th1$m$, and Th1$f$ can be selected by a selecting circuit 606 by an instruction of the CPU 601 on the basis of a set selection code SC1. A magnitude of the selected threshold value Th1 is compared with that of the output AD1 of the A/D converter by the comparator 607. When AD1>Th1, a code indicative of the presence of the defect and a defect data value AD1 are outputted as a discrimination result Df1. As for the SC1, the selection of the threshold value can be set in accordance with an examination object in such a manner that in the case of detecting a size of a designated size or larger, Th1$f$ is selected, in the case of examining by the optimum threshold value according to the surface state of the object to be examined, Th1$r$ is selected, and in the case of designating the examination sensitivity every region of the object to be examined, Th1$m$ is selected, respectively.

Embodiment 2

An example of an optical system construction in the case of four detectors and distribution of the reflection/scattering light from the sample is shown in FIG. 7. The reflection/scattering light from the sample 8 by the light irradiated to the sample 8 by an illuminating lens 7$b$ is converted into electric signals by the detectors 22, 32, 42, and 72 through the detection lenses 21, 31, 41, and 71 arranged at positions which are spatially independent of each other, respectively. As for intensities of the signals which are outputted from the detectors 22, 32, 42, and 72, magnitude distribution differs every signal intensity distribution maps D1$s$, D2$s$, D3$s$, and D4$s$ in dependence on the surface state, a crystal structure, or the like of the sample. A state of the large signal intensity is shown by regions (1), regions (2), regions (3), and regions (4) every signal intensity distribution maps D1$s$, D2$s$, D3$s$, and D4$s$ shown in the lower half portion in FIG. 7. Since the threshold value is formed in accordance with the signal intensity by the function of the discrimination processor in FIG. 6, the whole surface of the sample can be examined under the optimum condition irrespective of the state of the sample. Each of the detectors 22, 32, 42, and 72 fetches the signal of the whole surface of the sample and can examine by the optimum threshold value corresponding to the signal intensity.

Embodiment 3

Figure 11:
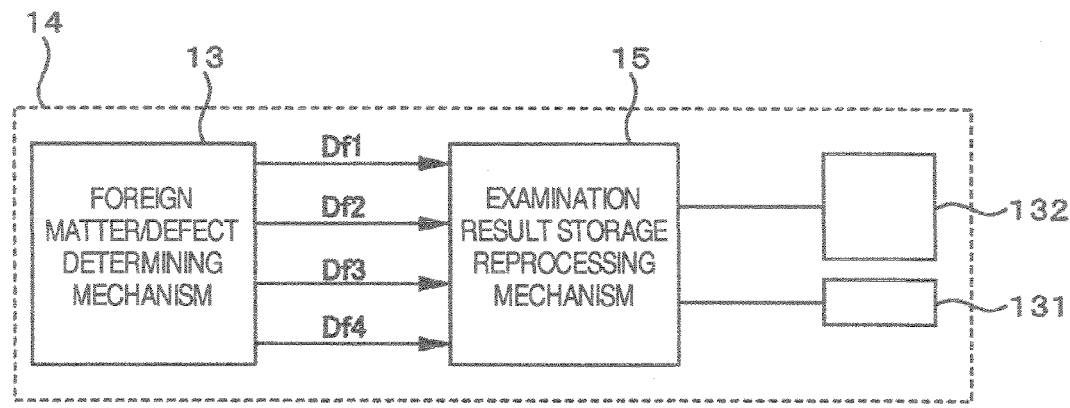
[FIG. 11] Explanatory diagram showing an example of a signal processing unit for reprocessing signal processing results in the case of three detectors by an arbitrary condition in the embodiment of the invention.

A reprocessing construction in the case of three detectors is shown in FIG. 11. Detection results of every three detectors and in the addition signal of the three detectors are outputted as four files Df1 to Df4 from the foreign matter/defect determining mechanism 13 and are stored into a detection result storage reprocessing mechanism 15. The stored files are arithmetically operated under conditions set by the input unit 131 and stored as new files. As an arithmetic operating condition, for example, the following condition can be mentioned: a detection which is performed only by the detector (1); the AND of a detection which is performed by the detector (1) and a detection which is performed by the detector (3), or the like; the OR of a detection which is performed by either the detector (1) or the detector (2), or the like; a discrimination about whether a file size is larger or smaller than a designated defect size; a process in a designated defect size range; or the like. Both conditions based on the AND/OR and the defect size mentioned above can be also simultaneously applied. Since the detectors (1), (2), and (3) are spatially independent of each other, a difference of shapes or sizes of the foreign matters/defects is detected as a difference of azimuth, elevation angle, or scattering intensity of the scattering light. By executing the reprocess about the presence or absence of the detection in each detector and the defect size under the proper conditions, the foreign matters/defects can be classified.

[Application Example 1]

Figure 8:
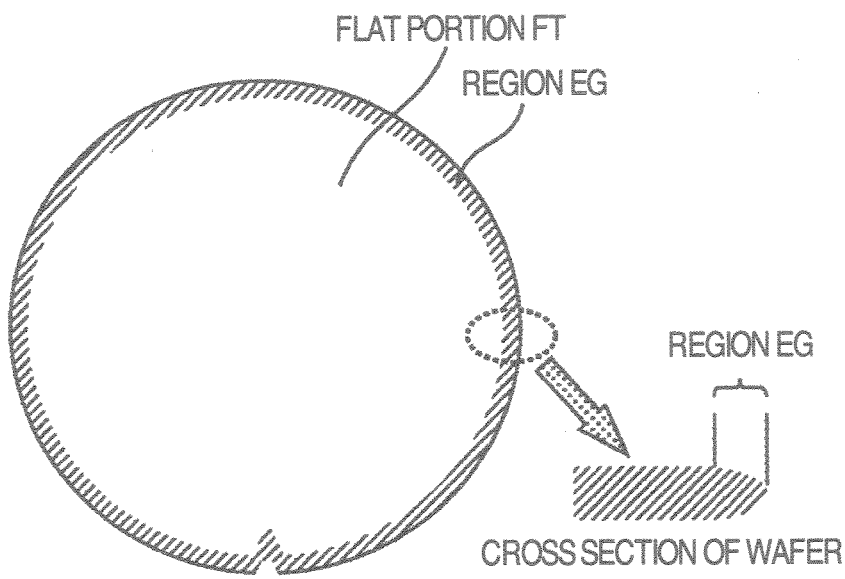
[FIG. 8] Explanatory diagram showing an example of an inclined region of an outer peripheral portion of a wafer in the embodiment of the invention.

An application example to the examination of the outer peripheral portion of the wafer will be described by using FIG. 8. According to the examination of a region EG (for example, bevel region) of the wafer outer peripheral portion, noises from the wafer cannot be largely examined by the same threshold value as that for a flat portion FT. A factor that the noises in the region EG of the outer peripheral portion of the wafer are large is that, mainly, the wafer is inclined and the surface state is rougher than the flat portion FT. In the region EG, in the detector in which the noises from the wafer are large, the optimum threshold value is calculated by the function described by using FIG. 6, the intensity (noise component) from the wafer surface is eliminated, and the examination can be performed without an erroneous detection. In the detector in which the incident light from the wafer surface is small, the proper threshold value is calculated by the function shown in FIG. 6 and the foreign matter/defect can be discriminated at a high sensitivity.

[Application Example 2]

Figure 9:
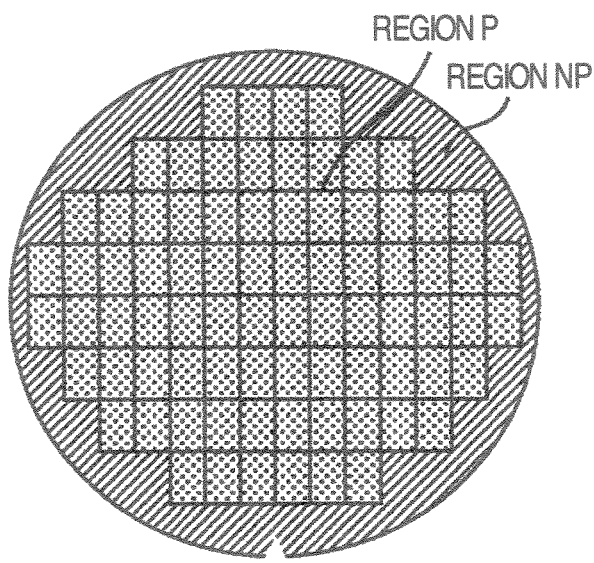
[FIG. 9] Explanatory diagram showing an example of a wafer with a pattern in the embodiment of the invention.

An application example to the examination of a wafer with a pattern will be described by using FIG. 9. As for the wafer with the pattern, in the case having a system construction using a rotary stage in which a scanning locus of an examination illumination is spiral or concentrical, the noises of the scattering light from the pattern varies depending on a rotational angle of the wafer. If the scattering light is converted into an electric signal by one detector, the noises are large in many regions of the wafer and the foreign matter/defect on the wafer cannot be discriminated or the detection sensitivity deteriorates remarkably.

However, by arranging a plurality of detectors at positions which are spatially different, calculating the optimum threshold value every region in correspondence to the noises from the wafer, and examining, in the chip forming region P where the chip has been formed, the detector in which the scattering light from the pattern is small exists. The proper threshold value is calculated by the function shown in FIG. 6 and the foreign matter/defect can be discriminated. Since no chip exists in the region NP where no chips are formed, the noises of the scattering light from the pattern are small, the examination threshold value is also automatically small, and the examination can be continuously performed. Since the threshold value is automatically formed in accordance with the intensity of the scattering light from the wafer, the examination can be performed by the same scanning sequence irrespective of the layout pattern of the region P and the region NP or the region ratio. The number of wafers which are processed can be increased.

Since a comparison of the chip data is not used in the detection processing logic, there is no need to input information such as chip size, layout, and the like as examination conditions and the optimum value of the examination threshold value is automatically calculated by the function shown in FIG. 6, a working time necessary to decide the examination conditions can be fairly shortened. As shown in FIG. 7, the foregoing process is simultaneously executed by a plurality of detectors in accordance with the detection signal and results of the detectors are added and outputted in a manner similar to the detection result of each detector.

[Application Example 3]

Figure 10:
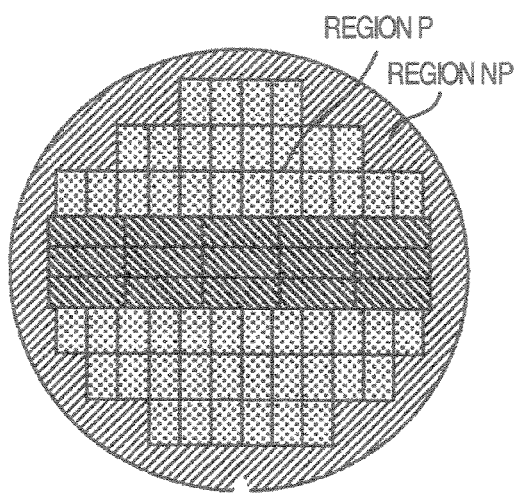
[FIG. 10] Explanatory diagram showing an example of a wafer with another pattern in the embodiment of the invention.

An application example to the examination of a wafer with another pattern will be described by using FIG. 10. Since there is no need to input the information such as chip size, layout, and the like as examination conditions as described in the Application Example 2, if the layout of the chips is not a matrix shape (hound's tooth check), different kinds of chips exist mixedly, or even in both of those examination samples, the proper threshold values are calculated for the respective detectors arranged at the positions which are spatially different and for the respective examination regions (region P and region NP). The foreign matter/defect can be discriminated irrespective of the state of the sample surface.

As mentioned above, in the Description, for example, there is disclosed such a technique that by setting the different threshold values every regions in accordance with the magnitude of the noises for each region of the object to be examined, it is possible to cope with a change in surface state and the detection sensitivity can be improved. Further, since the detection sensitivity is improved only by the reduction of the noise level, in the case of a micro defect whose detection recall factor is small due to the noise fluctuation, since the recall factor of the detection signal is improved by the improvement of the sensitivity, a size variation can be also improved.

For example, such a technique that the function for setting the examination threshold value every region is installed and the function for setting the examination threshold values for the plurality of detectors which are spatially independent of each other is installed in the optical examination device is also disclosed.

For example, such a technique that by paying an attention to a point that the magnitude of the noises from the object to be examined differs depending on the spatial direction even in the same region and the detection sensitivity can be maximized by maximizing the S/N ratio of the detection signal by the optimum signal arithmetic operating process and setting the optimum threshold value in accordance with the magnitude of the noises from the object to be examined every detector and every region of the object to be examined and by setting the optimum threshold value is disclosed.

Although the noises from the object to be examined vary every region depending on the surface state and crystalline structure of the object to be examined, the S/N ratio of the detection signal can be maximized by the optimum signal arithmetic operating process and the optimum threshold value can be set without being influenced by such a change, and the improvement of the detection sensitivity can be realized is disclosed.

Further, for example, the following features are disclosed.
1. An examination device comprising: an illuminating system for illuminating illumination light to an object to be examined; a detecting unit for detecting scattering light from the object to be examined; a plurality of detectors which are spatially independent of each other; and a signal processing unit for processing each output signal of the plurality of detectors by an independent processing condition.
2. The examination device according to the above paragraph 1, wherein the signal processing unit for processing by the independent processing condition has a discrimination processing unit for independently setting a threshold value every detector among the plurality of detectors and performing a discriminating process.
3. The examination device according to the above paragraph 1, wherein the signal processing unit for processing by the independent processing condition has a discrimination processing unit for changing a threshold value adapted to discriminate noises and a defect every detector among the plurality of detectors and every individual region of the object to be examined and performing a discriminating process.
4. The examination device according to the above paragraph 1, further comprising a display unit for arbitrarily selecting each output signal of the plurality of detectors and results of the signal processes and displaying into a same display screen.
5. The examination device according to the above paragraph 1, further comprising a signal processing unit for reprocessing signal processing results of the plurality of detectors by an arbitrary condition.
6. The examination device according to the above paragraph 1, wherein in the signal processing unit, a gain setting value adapted to maximize an S/N ratio of an addition result signal of output signals from the plurality of detectors is calculated and the value is set into the plurality of detectors.
7. An examination method of illuminating illumination light to an object to be examined and examining the object, comprising the steps of: detecting scattering light from the object to be examined by a plurality of detectors which are spatially independent of each other; and processing each output signal of the plurality of detectors by an independent processing condition.
8. The examination method according to the above paragraph 7, wherein upon processing by the independent processing condition, a threshold value is independently set every detector among the plurality of detectors and a discriminating process is performed.
9. The examination method according to the above paragraph 7, wherein upon processing by the independent processing condition, a threshold value adapted to discriminate noises and a defect is changed every detector among the plurality of detectors and every individual region of the object to be examined and a discriminating process is performed.
10. The examination method according to the above paragraph 7, wherein each output signal of the plurality of detectors and results of the signal processes are arbitrarily selected and displayed into a same display screen.
11. The examination method according to the above paragraph 7, wherein results of the signal processes of the plurality of detectors are reprocessed by an arbitrary condition.
12. The examination method according to the above paragraph 7, wherein a gain setting value adapted to maximize an S/N ratio of an addition result signal of output signals from the plurality of detectors is calculated and the value is set into the plurality of detectors.

The invention is not limited to the foregoing embodiments but various modifications are possible within a scope of its technical idea. For example, the invention is also applied to a case where there is a wall interface of a crystal in a predetermined direction like an epitaxial wafer. In this case, it is sufficient to construct in such a manner that the information of the detector which has outputted the smallest one of the signals detected from the independent detectors is selected and the examining process is executed. This is because since the scattering light due to the wall interface of the crystal ought to have characteristics in an azimuth manner, it is possible to expect that any one of the plurality of detectors arranged so as to cover the whole azimuth does not detect the scattering light due to the wall interface of the crystal.

REFERENCE SIGNS LIST

1 Light source
2 Amount-of-light adjusting mechanism
3 Optical axis compensating mechanism
5 Zoom mechanism
6a Vertical/oblique irradiation switching mirror
7a Focusing lens
8 Sample
9 XYZθ stage
10 Detection lens
11 Detector
12 A/D converter
13 Foreign matter/defect determining mechanism
131 Input unit
132 Output unit

The invention claimed is:

1. An inspection apparatus comprising:
an illumination system which supplies a sample with light;
a plurality of detectors which are spatially independent of each other, and output signals;
a processing unit which is configured to perform the following:
  detect noise signals of the signals,
  acquire a minimum value of the noise signals,
  acquire a plurality of gain values for the signals on the basis of the minimum value,
  acquire processed signals on the basis of the signals and the gain value, and
  detect a defect on the basis of at least one of the processed signals.

2. The inspection apparatus according to claim 1, wherein the processing unit is further configured to acquire a threshold value as a function of intensity of the signal.

3. The inspection apparatus according to claim 2, wherein the processing unit is further configured to:
integrate the processed signals,
acquire an integrated signal, and
detect the defect on the basis of the integrated signal.

4. The inspection apparatus according to claim 3, further comprising:
a rotating unit which rotates the sample,
wherein a pattern is formed on the surface of the sample.

5. The inspection apparatus according to claim 1, wherein the processing unit is further configured to:
integrate the processed signals,
acquire an integrated signal, and
detect the defect on the basis of the integrated signal.

6. The inspection apparatus according to claim 1, further comprising:
a rotating unit which rotates the sample,
wherein a pattern is formed on the surface of the sample.

7. An inspection method comprising steps of:
supplying a sample with light by way of an illumination system;
outputting signals by way of a plurality of detectors which are spatially independent of each other;
a processing unit which is configured to perform the following steps:
  detecting noise signals of the signals,
  acquiring a minimum value of the noise signals,
  acquiring a plurality of gain values for the signals on the basis of the minimum value,
  acquiring processed signals on the basis of the signals and the gain value, and
  detecting a defect on the basis of at least one of the proceed signals.

8. The inspection method according to claim 7, wherein the processing unit is further configured to perform the step of acquiring a threshold value as a function of intensity of the signal.

9. The inspection method according to claim 8, wherein the processing unit is further configured to perform the steps of:
integrating the processed signals,
acquiring an integrated signal, and
detecting the defect on the basis of the integrated signal.

10. The inspection method according to claim 9, further comprising the steps of:
rotating the sample by way of a rotating unit, and
forming a pattern on the surface of the sample.

11. The inspection method according to claim 7, wherein the processing unit is further configured to perform the steps of:
acquiring an integrated signal, and
detecting the defect on the basis of the integrated signal.

12. The inspection method according claim 7, further comprising the steps of:
rotating the sample by way of a rotating unit, and
forming a pattern on the surface of the sample.

* * * * *